(12) United States Patent
Knox

(10) Patent No.: US 7,161,048 B2
(45) Date of Patent: Jan. 9, 2007

(54) METHOD FOR DERIVING METHANOL FROM WASTE GENERATED METHANE AND STRUCTURED PRODUCT FORMULATED THEREFROM

(75) Inventor: Walter R. Knox, deceased, late of Chesterfield, MO (US); by Carol Knox, legal representative, Chesterfield, MO (US)

(73) Assignee: Rinnovi, L.L.C., St. Louis, MO (US)

( * ) Notice: Subject to any disclaimer, the term of this patent is extended or adjusted under 35 U.S.C. 154(b) by 0 days.

(21) Appl. No.: 11/382,923

(22) Filed: May 11, 2006

(65) Prior Publication Data

US 2006/0264683 A1  Nov. 23, 2006

Related U.S. Application Data

(60) Provisional application No. 60/683,040, filed on May 20, 2005.

(51) Int. Cl.
- C07C 27/10 (2006.01)
- C07C 41/02 (2006.01)
- C07C 27/00 (2006.01)
- C07C 37/00 (2006.01)

(52) U.S. Cl. .................. 568/911; 568/910; 568/910.5; 568/876; 568/806

(58) Field of Classification Search ........ 568/910–911, 568/876, 806
See application file for complete search history.

(56) References Cited

U.S. PATENT DOCUMENTS

| 1,945,353 | A | 1/1934 | Jaeger |
| 4,327,190 | A | 4/1982 | Ball et al. |
| 4,492,773 | A | 1/1985 | Ball et al. |
| 4,605,776 | A | 8/1986 | Kamiguchi et al. |
| 4,666,945 | A | 5/1987 | Osugi et al. |
| 4,723,041 | A | 2/1988 | Vasilevskis et al. |
| 5,196,634 | A | 3/1993 | Washecheck et al. |
| 5,233,113 | A | 8/1993 | Periana et al. |
| 5,306,855 | A | 4/1994 | Periana et al. |
| 5,345,011 | A | 9/1994 | Durante et al. |
| 5,478,962 | A | 12/1995 | DeNardo et al. |
| 5,786,505 | A | 7/1998 | Camaioni et al. |
| 6,538,162 | B1 | 3/2003 | Chang et al. |
| 6,869,578 | B1 | 3/2005 | Hebert et al. |
| 2003/0120125 | A1 | 6/2003 | Periana et al. |
| 2005/0154068 | A1 | 7/2005 | Hershkowitz et al. |
| 2005/0172553 | A1 | 8/2005 | Zartenar et al. |
| 2006/0025628 | A1 | 2/2006 | Zerella et al. |

FOREIGN PATENT DOCUMENTS

| DE | 3101024 | 8/1982 |
| EP | 0534545 | 3/1997 |

(Continued)

OTHER PUBLICATIONS

Crabtree, Robert H.; "Aspects of Methane Chemistry;" Journal—Chem Rev.; 1995; pp. 987-1007; 1995 American Chemical Society.

Primary Examiner—J. Parsa
(74) Attorney, Agent, or Firm—Blackwell Sanders Peper Martin LLP; Samuel Digirolamo

(57) ABSTRACT

Methanol is produced from bacterially oxidized waste methane by reaction with $Pd^{+2}$, $Cu^{+2}$, air, and molten phthalic anhydride in an entrained oxidizer generating half ester of methyl phthalate which is reaction distilled to produce methanol and recycle phthalic anhydride containing the $Pd^{+2}$, $Cu^{+2}$ phthalate catalyst.

20 Claims, 1 Drawing Sheet

FOREIGN PATENT DOCUMENTS

| | | |
|---|---|---|
| RU | 2189968 | 9/2002 |
| WO | 03031380 | 4/2003 |
| WO | 2004069784 | 8/2004 |
| WO | 2005037746 | 4/2005 |
| WO | 2005095313 | 10/2005 |

Figure 1. Process Flow Diagram

METHOD FOR DERIVING METHANOL FROM WASTE GENERATED METHANE AND STRUCTURED PRODUCT FORMULATED THEREFROM

CROSS REFERENCE TO RELATED APPLICATION

This application claims the benefit of U.S. provisional application Ser. No. 60/683,040, filed May 20, 2005 the disclosure of which is incorporated herein by reference.

BACKGROUND OF THE INVENTION

Methanol manufacture from methane via methane to synthesis gas ($CO+H_2$), and then synthesis gas to methanol is the current good, efficient, commercial way to make methanol. It becomes quite economic when performed on a big scale and using natural gas which is relatively free from inert non-hydrocarbon components. Conventional, small plants cannot compete well for capitol which becomes relatively high per unit of methanol produced. System pressure and need for compressors to raise pressure to 700–2500 psig is costly on a small scale. Today, methanol plants of over a billion pounds per year are desired. Whereas, 500 million pounds per year from waste methanol generation is about a maximum. Further, solid waste landfill assay gas will be about 50% carbon dioxide and 5% inerts (mainly nitrogen but with sulfur components, etc.). Carbon dioxide may be conveniently removed by one of several techniques which may also remove sulfur impurities. However, residual $N_2$ in methane is expensive to remove, generally via cryogenic distillation. Thus, a way to use methane without removing nitrogen or doing major compression in making methanol on the scale of solid waste landfills is desirable.

As more and more gas has been discovered in places removed from convenient pipelining, its conversion to methanol—a liquid easily shipped by tanker—has become a major choice use for this high methane natural gas. Three factors impact this product.

This gas product must be imported affecting balance of trade for importing country.

It comes to ports by tanker and requires trans-shipping to inland sites thus adding an additional cost.

Natural gas is not a "regenerable" quantity.

Thus, the conversion of solid waste landfill methane to methanol has some advantage, but the problems of scale, inerts and compression exist.

SUMMARY OF THE INVENTION

What is proposed herein is a technique to make methanol with less capitol per unit; methanol on a small scale while avoiding major compression and reacting methane away with simple cheap separations from nitrogen or other inerts.

The most advantageous method is to directly oxidize methane to methanol. The chemistry has long been recognized: $CH_4+[O] \rightarrow CH_3OH$. But unfortunately, many hundreds of efforts to stop there have been unsatisfactory. Simply put, each step in the oxidation

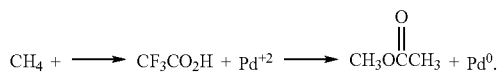

is easier than the step before. No adequate stopping has been set. In a multi-step rather expensive way, mercury complexes have worked. Economics for this have proved unattractive, but a second reaction preventing the oxidation pattern above functioned. This study [1]) has progressed to the system

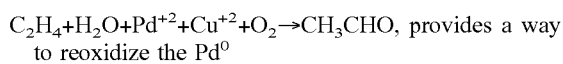

These investigators have recognized that the Wacker reaction:

$C_2H_4+H_2O+Pd^{+2}+Cu^{+2}+O_2 \rightarrow CH_3CHO$, provides a way to reoxidize the $Pd^0$ made to $Pd^{+2}$ via $Cu^{+1}+O_2 \rightarrow Cu^{+2}$, $2Cu^{+2}+Pd^0 \rightarrow 2Cu^{+1}+Pd^{+2}$. But although the high acidity of trifluoroacetic acid ($CF_3CO_2H$) allows esterification at rates (with ratios of components used) stopping oxidation toward formaldehyde, the ester must be very cheaply reconverted to methanol and recycle acid. The trifluoroacetic acid is expensive however the methanol product being made is quite cheap. Very little of the trifluoroacetic acid loss can be afforded.

Clearly if a stopping agent is to be used for the methane reaction commercially, it needs to be cheap and its conversion to methanol and the stopping agent very easy and cheap.

Phthalic anhydride is the preferred stopping agent. As a hot melt, phthalic anhydride reacts very readily and without catalyst to the half ester with methane.

Thus, the reaction,

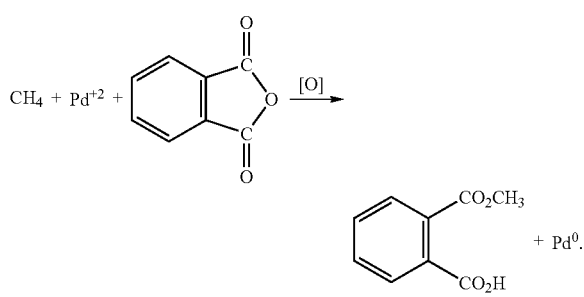

Of course, we must add copper as in the Wacker reaction and air for copper oxidation:

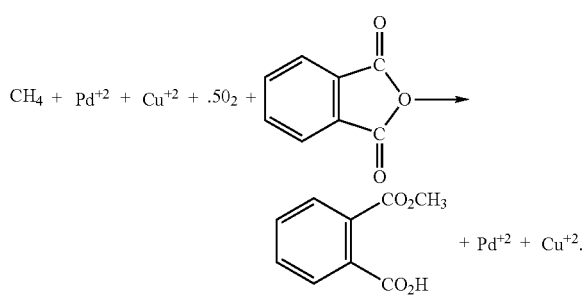

So, the $Pd^{+2}$, $Cu^{+2}$ becomes the catalyst and the reaction has only anhydride, methane and oxygen. The half ester is converted to phthalic anhydride and methanol by a temperature increase.

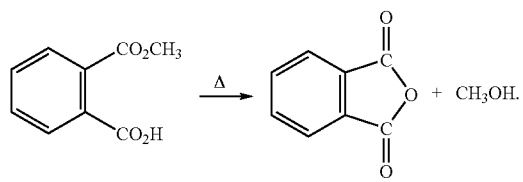

Phthalic anhydride is made by oxidizing naphthalene or o-xylene with vanadium catalyst at ~470° C. Similar conditions oxidize benzene to maleic anhydride. A C—H bond in benzene and that of methane have similar bond strength. Ergo, phthalic anhydride is indeed more oxidation stable than methane.

Most useful is the fact that dicarboxylic acids upon distillation are converted to the cyclic anhydride if the number of carbon atoms plus one oxygen creates a 5 or 6 membered ring. Thus maleic acid is converted commercially to maleic anhydride in an azeotropic distillation with xylene (right boiling point):

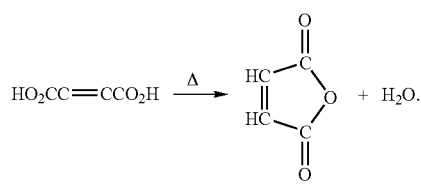

Water is the leaving group. Methanol has been seen to serve equally well as the leaving group:

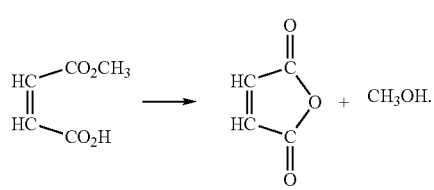

Likewise, phthalic acid and monomethyl phthalate will behave like maleic specie above. Thus,

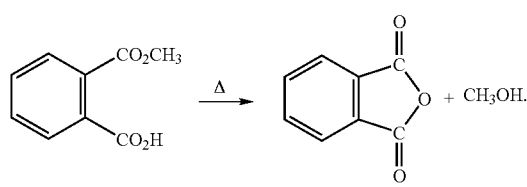

Now, the flow sheet may be understood.

DETAILED DESCRIPTION OF THE DRAWINGS

Figure 1:
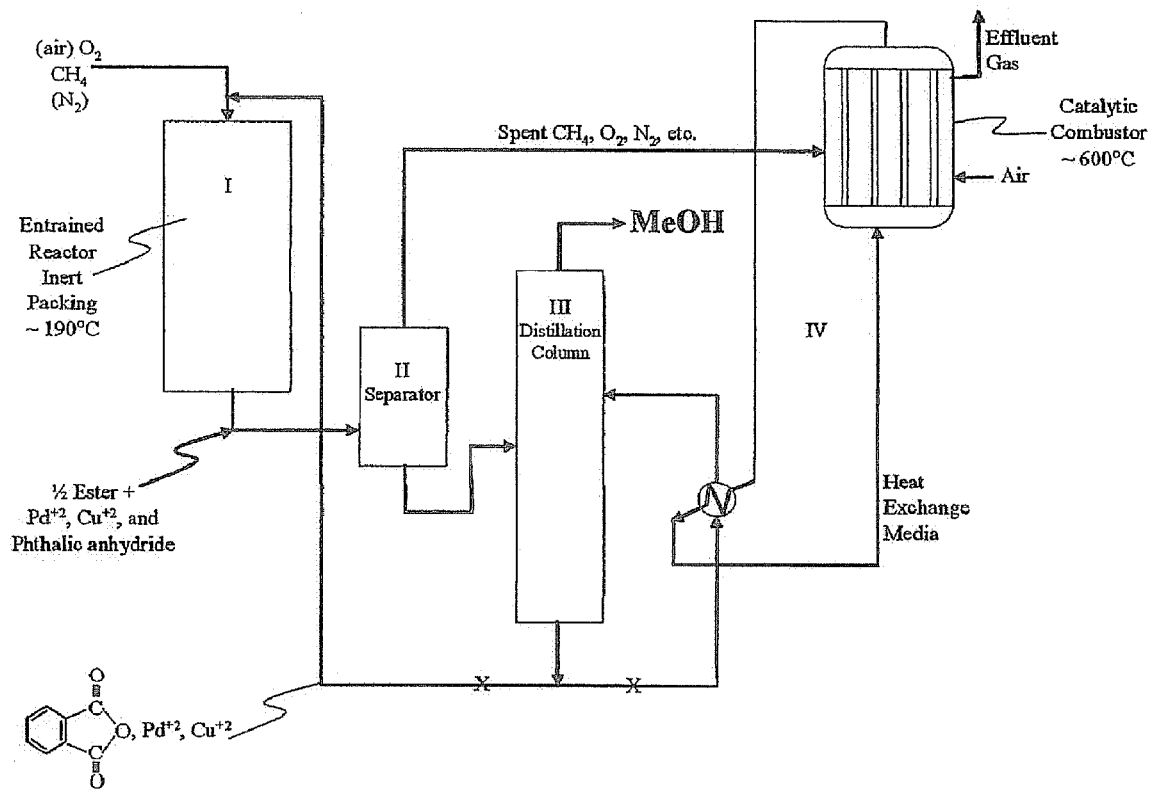
FIG. 1 is a schematic of the preferred embodiment of the present process for deriving methanol from methane.

In FIG. 1 there is shown an entrained reactor 1 with inert packing material. Methane gas is introduced to the reactor together with an anhydride of a dicarboxylic acid wherein the anhydride ring contains 4 or 5 carbon atoms. Preferably the diacid anhydride is phthalic anhydride. Air is also introduced into the reactor which is typically maintained at about 190° C. The reaction product, including the desired half ester methyl phthalate, is shown as leaving the reactor 1 via the bottom to a separator II wherein the unreacted methane and other gases are separated as top effluent and the liquid remainder leaving as a bottoms product to a distillation column III. The temperature of column III is maintained above the decomposition temperature of the half ester methyl phthalate thereby releasing methanol as an overhead product. In the preferred embodiment, the unreacted methane from separator II is forwarded to a catalytic combustor IV wherein the methane is catalytically converted to methanol and returned to column III via pipes and valves shown in FIG. 1. Also, the recovered phthalic anhydride from the bottom of column III is returned to reactor I for reuse in the process. Also shown in FIG. 1 is piping through which a heat exchange media is conducted to the catalytic combustor IV thereby recovering heat from this unit for use in the other units of the process requiring added heat to maintain desired temperature.

DETAILED DESCRIPTION OF THE INVENTION

To gain the conversion level needed for this once through oxidation at modest pressure, an entrainment reactor is preferred. This entrainment carries bubbles of gas down the reactor. Linear velocity of melted (i.e. liquid) phthalic anhydride entrains both methane and air such that as this liquid phase reacts with dissolved oxygen and methane, these gases are replaced by dissolving bubbles. In order to work well, an inert packing is used in reactor to provide continuous mixing with a modest pressure drop. Re-dissolving entrained gases allows use to work at moderate pressure and yet supply as much reactant to catalyst as a considerably higher pressure in which all reactant is pre-dissolved. The effect is as if we utilized the much higher pressure, more capital intensive system. The process functions by switching our first reactor to one utilizing oxidation to methanol and then very fast stabilization by the production of the half ester in excess, hot phthalic anhydride. The flow system with constant regeneration of $Pd^{+2}$ by $Cu^{+2}$ reaction with $Pd^0$ provides a high ratio of $Pd^{+2}$ to dissolved methane. Also, this reaction takes place at a fairly hot temperature. Thus methane oxidation is relatively fast and is not an equilibrium-regulated reaction by pressure.

To decompose the monomethyl phthalate, simply raise the temperature above its decomposition point. By utilizing good heat exchange in the distillation column methanol is taken overhead while returning phthalic anhydride via column bottoms, including $Pd^{+2}$, $Cu^{+2}$ phthalates to entrained oxidation. Total oxygen should always be less than enough for explosion, i.e. mixture remains hydrocarbon rich at all places. It may also be noted that this process causes nitrogen from the input gas stream to exit with unreacted methane and oxygen plus the nitrogen and small amounts of inerts from air inputs. Small levels of $H_2S$ or low boiling sulfur compounds will exit as occurring or be oxidized with this stream in the catalytic oxidizer. Several versions of this unit are possibilities including commercial waste oxidizers. A likely choice would be a Pt or alumina catalyst operating at about 600–700° C. This unit would provide the heat for the reactive distillation column. Generally speaking, entrained oxidation reactors will leave more B.T.U. value than reheat needs. However, if optimum conversion does not leave enough B.T.U. in entrained oxidation reactor vent gas and at high enough temperature, one can intentionally increase methane to waste burner by air decrease to entrainment reactor or by decreasing contact time.

We have an unusual economic situation. Methane cost in gas will be ½ to ¼ or less than the off shore big volume natural gas to competitive conventional facilities for methanol. Thus, balance on capitol and raw material will be more focused on capital. It will not be advantageous to waste gas, yet, in balance, capital restraint will have a larger role. It is essential, however, that we eliminate hydrocarbons from the environment via the catalytic combustor.

Given this overall picture, we can see lack of high pressure and simple capital systems allow a methanol reactor of relatively small size to be of good economics in the waste generated case.

Noble metals are intended to mean herein palladium, platinum, gold, silver, iridium, rhenium, mercury, ruthenium, and osmium. Preferred noble metals are palladium and platinum.

Although discussion has focused on methane generated within solid waste landfills after they are sealed as feed to modest methanol facilities, it should be recognized that bacterial decomposition in sewage disposal plants can also generate sizable methane. These facilities may also be raw material source for methane generation with this process. Yet another source of bacterial generation of methane for this process may be animal feces where large quantities of chicken or other fowl or livestock such as pigs or cattle are collectively raised for food supplies. Although assay of methane will vary with each source, generally a practical sized bacterial unit will regionally supply regenerable methane in quantities that are small compared to natural gas sources. Such small methane sources will basically fit the methanol system defined herein.

EXAMPLE 1

Utilizing the principles described in the summary, a waste methane input stream previously depleted of $CO_2$ and sulfur containing gases is oxidized in an entrainment reactor utilizing molten phthalic anhydride as the solvent/reactant. Air is the source of oxygen for the system with nitrogen, carbon dioxide, and its minor components present. The waste methane input stream is derived from solid waste landfill bacterial decomposition and, as stated, has had carbon dioxide, hydrogen sulfide, methyl and ethyl mercaptan removed along with traces of higher mercaptans. The stream contains an average assay of 5% nitrogen. Oxidation takes place in the presence of 2% palladium and 2% copper phthalate in the phthalic anhydride solution.

Flow rates involve about 85% molten phthalic solution and the remainder entrained and dissolved air and methane. Air quantity is such that methane to oxygen ratio is maintained at 0.3 mol oxygen/mol methane. Contact time for the total mix of liquid and gases is about one minute, temperature is 180–190° C. and pressure is about 150 psig inlet. Reactor is packed with non porous alpha alundum spheres of approximately ⅛" diameter.

Reactor effluent is fed to a separator of two theoretical trays which are also packed with alundum spheres as is the reactor. Separator bottoms are retained as an all liquid phase with maintenance of reactor exit temperature. The liquid phase from separator bottom is charged about mid way to a distillation column. Column bottoms are split and about half recycled to column entry about 60% up column as reboiler via heat exchanger such that entry liquid from reboiler raises full charge to about 210–220° C. That portion of column bottoms not sent in column recycle is sent back to entrainment reactor to pick up gases again after pumping it back to 150 psig.

Reaction distillation column tops contain primarily methanol. This methanol may be redistilled to separate trace impurities, e.g. water from small over-oxidation.

The once through tops stripped from the half ester, anhydride catalyst bottoms are composed of methane, nitrogen and miscellaneous small components from air and the waste methane input stream. They are sent to a bed of two percent platinum metal dispersed on an active alumina of about 250 sq.m./g, surface area. Air is preheated in stainless steel coils immersed in the oxidation catalyst bed, then sent back to enter the bed with vent gases from the entrained oxidation reactor. Preheated air is used in a quantity to make the ratio of about 3 mols oxygen to 1 mol of methane. Mixed gas temperature entering this catalytic combustor will be 400–450° C. Terphenyl mixture heat exchange fluid also is passed through its catalytic combustor in tubes. It's velocity and quantity will be adequate to keep its tube temperature less than 350° C. and exiting fluid about 275–300° C. This terphenyl is used to heat exchange with reboiler of the reaction/distillation system before the latter is recharged to that system's column.

Total reaction system is continuous and will be on stream around the clock until maintenance is needed. For the example we will utilize a ten minute period after system conditions are in balance. In that time we make methanol as defined above.

A flow diagram delineating the process described in EXAMPLE 1 is provided in FIG. 1. The diagram traces the flow of waste methane process gas and catalysts through the entrained packed bed reaction (I) and into a packed bed separator (II). Liquid bottoms from the separator are fed to the distillation column (III), while the gas stream is fed to the catalytic combustor/heat exchanger (IV).

Bottoms from the distillation column (III) are split, with approximately 50% reintroduced to the entrained packed bed reactor (I), and 50% reintroduced to the distillation column (III) after first being brought to temperature in the waste heat exchanger (IV).

EXAMPLE 2

Essentially, the same as EXAMPLE 1, but with ¾ mullite inert ceramic spheres and super heated steam used as the heat exchange medium in the catalytic combustion of effluent from ethane oxidation in the phthalate system. Again, methanol is made as the product.

EXAMPLE 3

Same as EXAMPLE 1, except methane is not pre-treated to remove $CO_2$ and any sulfur-containing components. Effluent will contain trace $SO_2$ from the catalytic combustor and the feed gas $CO_2$ as well as $CO_2$, $H_2$, $N_2$, etc., from air plus effluent at ~600° C. Product methanol will be essentially the same as EXAMPLE 1.

EXAMPLE 4

Same as EXAMPLE 3, except the waste methanol stream is derived from animal waste. This feed has less $N_2$ and $CO_2$ in it than EXAMPLE 3, hence more methane.

Variations or modifications to the subject matter of the formula and process, in addition to the compound formed, namely, methanol, may occur to those skilled in the art upon review of the invention as described herein. Such variations, if within the spirit of this development, are intended to be encompassed within the scope of the invention as defined. The description of the preferred embodiment, and its summarization within the application, are set forth for illustrative purposes only.

What is claimed is:

1. A process for producing methanol from methane gas comprising the steps of
   (a) Oxidizing methane in a reactor containing air and catalysts comprising a noble metal catalyst and copper and in the presence of a cyclic anhydride of a dicarboxylic acid containing from 4 to 5 carbon atoms in the anhydride ring to form the half methyl ester of said acid;
   (b) Subjecting the reaction product of step (a) to a stripping column to separate waste gases at the top of the column from the bottom product compositions in said reaction product; and
   (c) Subjecting the bottom compositions of step (b) to the decomposition temperature of the half methyl ester producing methanol.

2. The process of claim 1 wherein the anhydride is phthalic anhydride.

3. The process of claim 1 wherein the reactor in step (a) is an entrainment reactor containing an inert packing.

4. The process of claim 1 wherein the heat to provide the decomposition temperature is supplied by the combustion of residual methane from the reactor to step (a) in the presence of a noble metal catalyst.

5. The process of claim 1 wherein the methane gas entering step (a) is derived from waste gas containing methane.

6. The process of claim 3 wherein the inert packing comprises alpha alumina spheres having a diameter in the range of from about 1/16 to about 1/2 inch.

7. The process of claim 6 wherein the spheres have a surface area of less than 5 sq.m./g.

8. The process of claim 1 wherein step (c) is conducted in a reaction/distillation column and the methanol is an overhead effluent.

9. The process of claim 3 wherein the entrainment reactor is operated at a pressure in the range of from about 5 to about 400 psig.

10. The process of claim 1 further including the step of subjecting the waste gas from the top of the column in step (b) to a catalytic combustion reactor to convert unreacted methane to methanol in the presence of a noble metal catalyst.

11. The process of claim 10 wherein the noble metal catalyst is selected from the group consisting of platinum and a platinum/rhenium mixture.

12. The process of claim 11 wherein the catalyst is platinum in an amount in the range of from about 0.05% to about 3% and wherein the catalyst is a platinum/rhenium mixture the amount of platinum is at least about 0.4%.

13. The process of claim 10 wherein the noble metal catalyst is on an active support material, said material having a surface area of from about 50 to about 650 sq.m./g. and the noble metal is present in an amount of from about 0.5% to about 10% by weight of said support.

14. The process of claim 10 wherein the catalytic combustion reactor provides heat for a heat exchange media.

15. The process of claim 10 wherein the noble metal catalyst comprises from about 0.5% to about 10% by weight of the support material.

16. The process of claim 14 wherein the heat exchange medium is selected from the group consisting of biphenyl, terphenyl mixtures, mixed methyl naphthalenes and steam.

17. The process of claim 1 wherein the methane is derived from a bacterially produced source.

18. The process of claim 17 wherein the methane is derived from a landfill.

19. The process of claim 17 wherein the methane is the product of a sewage disposal plant.

20. The process of claim 17 wherein the methane is the product of animal feces.

* * * * *

UNITED STATES PATENT AND TRADEMARK OFFICE
CERTIFICATE OF CORRECTION

PATENT NO. : 7,161,048 B2
APPLICATION NO. : 11/382923
DATED : January 9, 2007
INVENTOR(S) : Walter R. Knox It is certified that error appears in the above-identified patent and that said Letters Patent is hereby corrected as shown below:

Col. 2, line 2, delete "set" and replace with -- seen --

Col. 4, line 41, delete "use" and replace with -- us --

Col. 6, line 41, delete "reaction" and replace with -- reactor --

Claim 4, Col. 7, line 37, delete "to step (a)" and replace with -- of step (a) --

Signed and Sealed this

Fourteenth Day of August, 2007

JON W. DUDAS
*Director of the United States Patent and Trademark Office*